United States Patent [19]
Dodd et al.

[11] Patent Number: 6,147,096
[45] Date of Patent: Nov. 14, 2000

[54] SUBSTITUTED PYRROLOBENZIMIDAZOLES FOR TREATING INFLAMMATORY DISEASES

[75] Inventors: John H. Dodd, Pittstown; James R. Henry, Bloomsbury; Kenneth C. Rupert, South Orange, all of N.J.

[73] Assignee: Ortho McNeil Pharmaceutical, Inc., Raritan, N.J.

[21] Appl. No.: 09/257,121

[22] Filed: Feb. 25, 1999

Related U.S. Application Data

[60] Provisional application No. 60/076,063, Feb. 26, 1998.

[51] Int. Cl.$^7$ ..................... C07D 401/04; A61K 31/4427
[52] U.S. Cl. ....................... 514/338; 514/333; 546/273.1; 546/256
[58] Field of Search ................................. 546/273.1, 256; 514/338, 333

[56] References Cited

FOREIGN PATENT DOCUMENTS

WO 93/14081  7/1993  WIPO .

OTHER PUBLICATIONS

C. Dinarello et al., Inflammatory cytokines: Interleukin–1 and Tumor Necrosis Factor as Effector Molecules in Autoimmune Diseases, *Curr. Opin. Immunol.* 1991, 3, 941–48.

M.J. Elliot et al., Treatment of Rheumatoid Arthritis with Chimeric Monoclonal Antibodies to Tumor Necrosis Factor α, *Arthritis Rheum.* 1993 36, 1681–90.

J.C. Boehm et al., 1–Substituted 4–Aryl–5–pyridinylimidazoles: A New Class of Cytokine Suppressive Drugs with Low 5–Lipoxygenase and Cyclooxygenase Inhibitory Potency, *J. Med. Chem.*, 1996, 39, 3929–37.

A.M. Badger, et al., Pharmacological Profile of SB 203580, A Selctive Inhibitor of Cytokine Suppressive Binding Protein/p38 Kinase, in Animal Models of Arthritis, Bone Resorption, and Immune Function, *The Journal of Pharmacology and Experimental Therapeutics*, 1996, 279, 1453–61.

Gallagher, T.F. et al., Regulation of Stress–Induced Cytokine Production by Pyridinylimidazoles; Inhibition of CSBP Kinase, *Bioorganic& Medicinal Chemistry*, 1997, 5, 49–64.

Chetverikov, V.P. et al., Synthesis of 2–imidazo[4,5–e]indoles from 5–aminobenzimidazoles, *Zhim. Geterotsiki. Soedin*, 1980, 1, 74–8.

Lantos, I. et al., Synthetic and Mechanistic Studies on the Preparation of Pyridyl–Substituted Imidazothiazoles, *J. Org. Chem.*, 1988, 53, 4223–27.

*Primary Examiner*—Jane Fan
*Attorney, Agent, or Firm*—Alan J. Morrison

[57] ABSTRACT

This invention provides compounds, and pharmaceutically acceptable salts thereof, having the structure shown below, as well as related pharmaceutical compositions, and methods of treatment and synthesis.

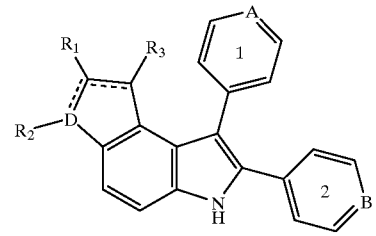

12 Claims, No Drawings

SUBSTITUTED PYRROLOBENZIMIDAZOLES FOR TREATING INFLAMMATORY DISEASES

This is application claims the benefit under 35 USC 119 e of provisional application No. 60/076,063, filed Feb. 26, 1998.

Throughout this application, various publications are cited. The disclosure of these publications is hereby incorporated by reference into this application to describe more fully the state of the art to which this invention pertains.

FIELD OF THE INVENTION

This invention relates to substituted pyrrolobenzimidazoles, and related pharmaceutical compositions and methods for treating inflammatory diseases. The compounds of the invention inhibit the production of cytokines, particularly TNF-α and IL-1, which mediate inflammatory responses.

BACKGROUND OF THE INVENTION

The inflammatory cytokines IL-1 and TNF-α play an important role in a number of inflammatory diseases. (C. Dinarello et al., Inflammatory cytokines: Interleukin-1 and Tumor Necrosis Factor as Effector Molecules in Autoimmune Diseases, *Curr. Opin. Immunol.* 1991, 3, 941–48.) Rheumatoid arthritis is a prime example of such inflammatory diseases, and is thus the inflammatory disease focused on most in this section.

Rheumatoid arthritis is an inflammatory disease which affects millions of people and can affect any joint in the human body. Its symptoms range from mild pain and inflammation in affected joints, to severe and debilitating pain and inflammation. Although the disease is associated mainly with aging adults, it is not restricted to adults.

The most common rheumatoid arthritis therapy involves the use of nonsteroidal anti-inflammatory drugs (NSAID's) to alleviate symptoms. However, despite the widespread use of NSAID's, many individuals cannot tolerate the doses necessary to treat the disease over a prolonged period of time. In addition, NSAID's merely treat the symptoms of disease without affecting the underlying cause(s). Other drugs, such as methotrexate, gold salts, D-penicillamine and prednisone are often used when patients fail to respond to NSAID's. These drugs also have significant toxicities and their mechanisms of action remain unknown.

Receptor antagonists to IL-1 and monoclonal antibodies to TNF-α have been shown to reduce symptoms of rheumatoid arthritis in small-scale human clinical trials. (M. J. Elliot et al., Treatment of Rheumatoid Arthritis with Chimeric Monoclonal Antibodies to Tumor Necrosis Factor α, Arthritis Rheum. 1993 36, 1681–90.)

In addition to protein-based therapies, there are small molecule agents which inhibit the production of these cytokines and have demonstrated activity in animal rheumatoid arthritis models. (J. C. Boehm et al., 1-Substituted 4-Aryl-5-pyridinylimidazoles: A New Class of Cytokine Suppressive Drugs with Low 5-Lipoxygenase and Cyclooxygenase Inhibitory Potency, *J. Med. Chem.*, 1996, 39, 3929–37.) Of these small molecule agents, SB 203580 has proven effective in reducing the production of TNF-α and IL-1 in LPS-stimulated human monocyte cell lines with $IC_{50}$ values of 50 to 100 nM. (J. Adams et al., Imidazole Derivatives And Their Use as Cytokine Inhibitor, International patent application WO 93/14081, 1993.)

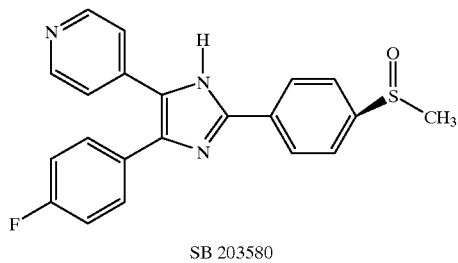

SB 203580

In addition to this in vitro behavior, SB 203580 has been shown to inhibit the production of inflammatory cytokines in rats and mice at $IC_{50}$ values of 15 to 25 mg/kg. (A. M. Badger, et al., Pharmacological Profile of SB 203580, A Selective Inhibitor of Cytokine Suppressive Binding Protein/p38 Kinase, in Animal Models of Arthritis, Bone Resorption, Endotoxin Shock and Immune Function, *The Journal of Pharmacology and Experimental Therapeutics*, 1996, 279, 1453–61.)

Due to SB 203580's oral activity and potency in animal models, researchers have suggested that a compound with this profile has potential as a viable treatment for rheumatoid arthritis. (A. M. Badger, et al. Pharmacological Profile of SB 203580, A Selective Inhibitor of Cytokine Suppressive Binding Protein/p38 Kinase, in Animal Models of Arthritis, Bone Resorption, Endotoxin Shock and Immune Function, *The Journal of Pharmacology and Experimental Therapeutics*, 1996, 279, 1453–61.)

SB 203580 and other small molecules reduce the production of inflammatory cytokines by inhibiting the activity of a serine/threonine kinase, p38 (also referred to in the art as "CSBP"), at an $IC_{50}$ of 200 nM. (D. Griswold et al., Pharmacology of Cytokine Suppressive Anti-Inflammatory Drug Binding Protein (CSPB), A Novel Stress-Induced Kinase, *Pharmacology Communications*, 1996, 7, 323–29.) Although the precise mechanism of this kinase is unknown, it has been implicated in both the production of TNF-α and the signaling responses associated with the TNF-α receptor.

Rheumatoid arthritis, and the host of other inflammatory disorders, take a severe toll on those afflicted. There is thus a tremendous need for small molecule anti-inflammatory agents. To date, however, no such agent—including SB 203580—has ever been shown to be anti-inflammatory in human clinical trials.

SUMMARY OF THE INVENTION

This invention provides a compound having the structure

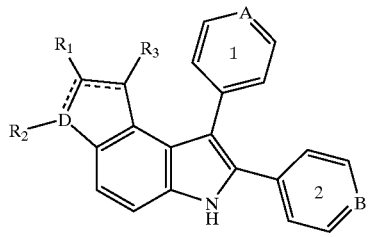

or a pharmaceutically acceptable salt thereof, wherein:

(a) $R_1$, $R_2$ and $R_3$ are independently selected from the group consisting of (i) hydrogen, (ii) $C_{1-5}$alkyl, (iii) $C_{1-5}$alkylamino, (iv) di$C_{1-5}$alkylamino, (v) a phenyl substituted with one or more of hydrogen, halogen, $C_{1-5}$alkyl, and trihalo$C_{1-5}$alkyl, and (vi) a phenyl$C_{1-5}$alkyl substituted with one or more of hydrogen, halogen, $C_{1-5}$alkyl, and trihalo$C_{1-5}$alkyl;

(b) rings 1 and 2 are each independently substituted with one or more substituents selected from the group consisting of hydrogen, halogen, $C_{1-5}$alkyl, and trihalo$C_{1-5}$alkyl;

(c) A and B are independently nitrogen or carbon, at least one of A and B being nitrogen;

(d) D and E are nitrogen, with the proviso that (i) a double bond exists between the non-aryl carbon and either D or E, (ii) $R_2$ is absent if the double bond exists between the non-aryl carbon and D, and (iii) $R_3$ is absent if the double bond exists between the non-aryl carbon and E; and (e) the compound is neither 1,6-dihydro-7-(4-pyridyl)-8-(4-fluorophenyl)-2-phenylmethyl-pyrrolo[3,2-e]benzimidazole, nor 3,6-dihydro-8-(4-fluorophenyl)-3-(3-phenylpropyl)-7-(4-pyridyl)-pyrrolo[3,2-e]benzimidazole.

This invention also provides a pharmaceutical composition comprising the instant compound, and a pharmaceutically acceptable carrier. This invention further provides a method of treating a subject having an inflammatory disease, which comprises administering to the subject a therapeutically effective dose of the instant pharmaceutical composition.

Finally, this invention provides a method of making the instant compound, which comprises the step of contacting a first compound having the structure

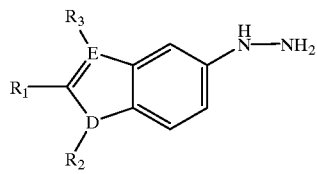

with a second compound having the structure

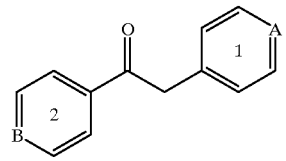

under conditions permitting a Fischer indolization between the first and second compounds.

DETAILED DESCRIPTION OF THE INVENTION

This invention provides compounds and related pharmaceutical compositions and methods useful in the treatment of inflammatory diseases. The compounds of the invention inhibit the production of the inflammatory cytokines TNF-α and IL-1β, the overproduction of which are characteristic of inflammatory diseases.

Specifically, this invention provides a compound having the structure

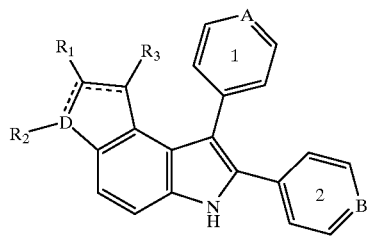

or a pharmaceutically acceptable salt thereof, wherein:

(a) $R_1$, $R_2$ and $R_3$ are independently selected from the group consisting of (i) hydrogen, (ii) $C_{1-5}$alkyl, (iii) $C_{1-5}$alkylamino, (iv) di$C_{1-5}$alkylamino, (v) a phenyl substituted with one or more of hydrogen, halogen, $C_{1-5}$alkyl, and trihalo$C_{1-5}$alkyl, and (vi) a phenyl$C_{1-5}$alkyl substituted with one or more of hydrogen, halogen, $C_{1-5}$alkyl, and trihalo$C_{1-5}$alkyl;

(b) rings 1 and 2 are each independently substituted with one or more substituents selected from the group consisting of hydrogen, halogen, $C_{1-5}$alkyl, and trihalo$C_{1-5}$alkyl;

(c) A and B are independently nitrogen or carbon, at least one of A and B being nitrogen;

(d) D and E are nitrogen, with the proviso that (i) a double bond exists between the non-aryl carbon and either D or E, (ii) $R_2$ is absent if the double bond exists between the non-aryl carbon and D, and (iii) $R_3$ is absent if the double bond exists between the non-aryl carbon and E; and (e) the compound is neither 1,6-dihydro-7-(4-pyridyl)-8-(4-fluorophenyl)-2-phenylmethyl-pyrrolo[3,2-e]benzimidazole, nor 3,6-dihydro-8-(4-fluorophenyl)-3-(3-phenylpropyl)-7-(4-pyridyl)-pyrrolo[3,2-e]benzimidazole.

In one embodiment of the instant compound, D and E are both nitrogen. In another embodiment, A is nitrogen and B is carbon. In still another embodiment, D, E and A are nitrogen and B is carbon. In the preferred embodiment of the instant compound, the compound is selected from the group consisting of (i) 1,6-dihydro-7-(4-fluorophenyl)-8-(4-pyridyl)-2-phenyl-pyrrolo[3,2-e]benzimidazole; (ii) 1,6-dihydro-7-(4-fluorophenyl)-8-(4-pyridyl)-2-butyl-pyrrolo[3,2-e]benzimidazole; (iii) 1,6-dihydro-7-(4-fluorophenyl)-8-(4-pyridyl)-2-(2-phenylethyl)-pyrrolo[3,2-e]benzimidazole; (iv) 1,6-dihydro-7-(4-pyridyl)-8-(4-fluorophenyl)-pyrrolo[3,2-e]benzimidazole; and (v) 1,6-dihydro-7-(4-fluorophenyl)-8-(4-pyridyl)-2-phenylmethyl-pyrrolo[3,2-e]benzimidazole.

As used herein, the terms below have the following meanings in relation to the instant compound: "independently", when in reference to chemical substituents, shall mean that when more than one substituent exists, the substituents may be the same or different; "alkyl" shall mean straight, cyclic and branched-chain alkyl; "alkoxy" shall mean O-alkyl; "halogen" shall mean fluorine, chlorine, bromine or iodine; and "Ph" shall mean phenyl.

Typically the instant compound is isolated and used as a free base. However, its various embodiments can also be isolated and used as pharmaceutically acceptable salts. Examples of such salts include hydrobromic, hydroiodic, hydrochloric, perchloric, sulfuric, maleic, fumaric, malic, tartaric, citric, benzoic, mandelic, methanesulfonic, hydroethanesulfonic, benzenesulfonic, oxalic, palmoic, 2-naphthalenesulfonic, p-toluenesulfonic, cyclohexanesulfamic and saccharic.

This invention also provides a pharmaceutical composition comprising the instant compound, and a pharmaceutically acceptable carrier.

Pharmaceutically acceptable carriers are well known to those skilled in the art and include, but are not limited to, 0.01–0.1 M and preferably 0.05 M phosphate buffer or 0.8% saline. Additionally, such pharmaceutically acceptable carriers can be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, ethanol, alcoholic/aqueous solutions, glycerol, emulsions or suspensions, including saline and buffered media. Oral carriers can be elixirs, syrups, capsules tablets and the like. The typical solid carrier is an inert substance such as lactose, starch, glucose, methyl cellulose, magnesium sterate, dicalcium phosphate, mannitol and the like. Parenteral carriers include sodium chloride solution, Ringer's dextrose, dextrose and sodium chloride, lactated Ringer's and fixed oils. Intravenous carriers include fluid and nutrient replenishers, electrolyte replenishers such as those based on Ringer's dextrose, and the like. Preservatives and other additives can also be present, such as, for example, antimicrobials, antioxidants, chelating agents, inert gases and the like. All carriers can be mixed as needed with disintegrants, diluents, granulating agents, lubricants, binders and the like using conventional techniques known in the art.

This invention further provides a method of treating a subject having an inflammatory disease, which comprises administering to the subject a therapeutically effective dose of the instant pharmaceutical composition.

As used herein, "subject" means any animal or artificially modified animal having an inflammatory disease. In the preferred embodiment, the subject is a human.

Inflammatory diseases are numerous and well known in the art. Examples of inflammatory diseases include, but are in no way limited to, rheumatoid arthritis, insulin-dependent diabetes mellitus, multiple sclerosis, myasthenia gravis, Crohn's disease, autoimmune nephritis, primary biliary cirrhosis, psoriasis, acute pancreatitis, allograph rejection, allergic inflammation, inflammatory bowel disease, septic shock, osteoporosis, osteoarthritis, and cognitive deficits induced by neuronal inflammation. In the preferred embodiment, the autoimmune disease is rheumatoid arthritis.

Administering the pharmaceutical composition can be effected or performed using any of the various methods known to those skilled in the art. The administering can be performed, for example, intravenously, intramuscularly, orally and subcutaneously. In the preferred embodiment, the instant pharmaceutical composition is administered orally. Additionally, the administering can comprise giving the subject a plurality of dosages over a suitable period of time which can be determined according to routine methods.

A "therapeutically effective dose" of the pharmaceutical composition means an amount sufficient to stop, reverse or reduce the progression of the inflammatory disease being treated. Methods are known in the art which can be used to determine therapeutically effective doses for administering the instant pharmaceutical composition in a subject. The effective dose for administering the pharmaceutical composition to a human, for example, would be determined mathematically from the results of animal studies. In one embodiment, the therapeutically effective dose is a dose sufficient to deliver from about 0.05 mg to about 200 mg of the instant pharmaceutical composition per kilogram of body weight daily. In another embodiment, the therapeutically effective dose is a dose sufficient to deliver from about 0.5 mg to about 50 mg.

Finally, this invention provides a method of making the instant compound, which comprises the step of contacting a first compound having the structure

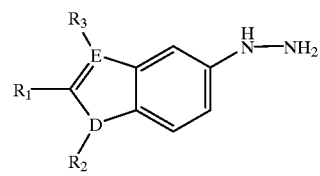

with a second compound having the structure

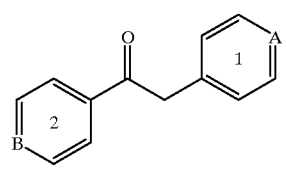

under conditions permitting a Fischer indolization between the first and second compounds. In the first and second compounds, the designations for the rings and ring substituents (i.e., rings 1 and 2, atoms A, B, D and E, and substituents $R_1$, $R_2$ and $R_3$) and definitions thereof, are the same as those used in connection with the instant compound described above. Conditions permitting Fischer indolizations are well known in the art, and are exemplified in the Experimental Details below.

This invention will be better understood by reference to the Experimental Details which follow, but those skilled in the art will readily appreciate that the specific experiments detailed are only illustrative of the invention as described more fully in the claims which follow thereafter.

EXPERIMENTAL DETAILS

A. Definitions

As used herein, the terms below shall have the following meanings in relation to the instant experimental methods: "FCS" shall mean fetal calf serum; "TCA" shall mean trichloroacetic acid; "RPMI" shall mean the medium from the Roswell Park Memorial Institute having Sigma Cat No. R0833; and "Formula I" shall mean the structure set forth below and defined above.

B. Syntheses

The compounds of this invention can be prepared by the following schemes, whereby some schemes produce more than one of the instant compounds. In those cases, the choice of scheme is a matter of discretion which is well within the capabilities of those skilled in the art.

1. Pyrrolobenzimidazole Ring System

As illustrated by Scheme 1, the pyrrolobenzimidazole ring system of compounds of Formula 1 is formed by coupling a 1,2-substituted ethanone, 1b, with an appropriately substituted 5-hydrazinobenzimidazole 1a, in a suitable solvent such as ethylene glycol at about 90° C. for about 1–3 hours to give the compound shown.

Aside from the illustrated product, many other compounds of Formula I can be produced by varying the starting materials 1a and 1b. A variety of substituted ethanones can be prepared by treating known benzamide derivatives with 4-picolyl anions. (Gallagher, T. F. et al., Regulation of Stress-Induced Cytokine Production by Pyridinylimidazoles; Inhibition of CSBP Kinase, *Bioorganic & Medicinal Chemistry*, 1997, 5, 49–64.) A variety of substituted hydrazinyl-benzimidazoles may be prepared by treating 5-amino benzimidazoles with nitrous acid and stannous chloride. (Chetverikov, V. P. et al., Synthesis of 2-imidazo[4,5-e]indoles from 5-aminobenzimidazoles, *Zhim. Geterotsiki. Soedin*, 1980, 1, 74–8.) Therefore, to prepare a compound of Formula I where A is nitrogen, B is carbon, ring 2 has a 4-fluoro substituent, and $R_1$ is methylphenyl, replace the illustrated 1a with 2-methyl-5-hydrazinobenzimidazole and 1b with 1-[4-fluorophenyl]-2-[4-pyridinyl]ethanone.

SCHEME 1

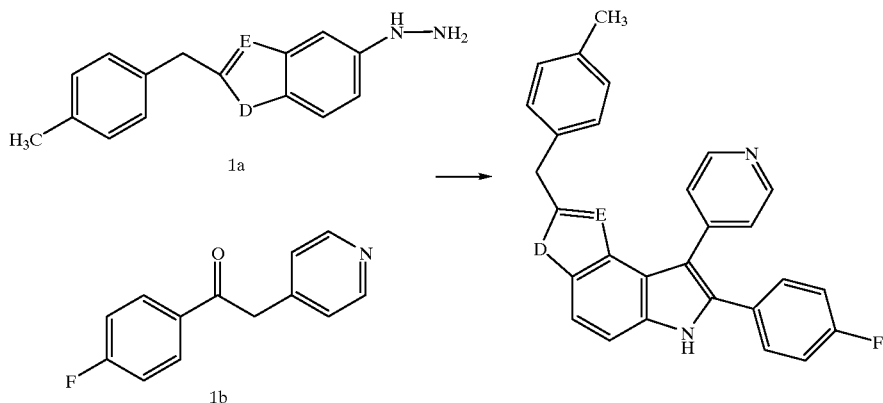

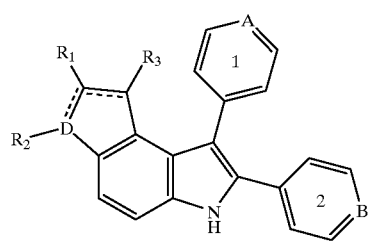

2. First Embodiment of Formula I

Scheme 2 can be used to prepare the compound of Formula I, wherein A is nitrogen, B is carbon, $R_3$ is ethyl, and $R_1$ is hydrogen. The starting substituted ethanone, 2b, is treated with a suitable 6-hydrazinobenzimidazole 2a, in a suitable solvent such as ethylene glycol at about 90° C. for about 1–3 hours to give the desired compound. Aside from the illustrated compound other compounds of Formula I can be prepared in this manner. The 6-hydrazinobenzimidazoles can be prepared from the 6-amino compounds using similar methods as described in the preparation of the 5-hydrazinobenzimidazoles.

SCHEME 2

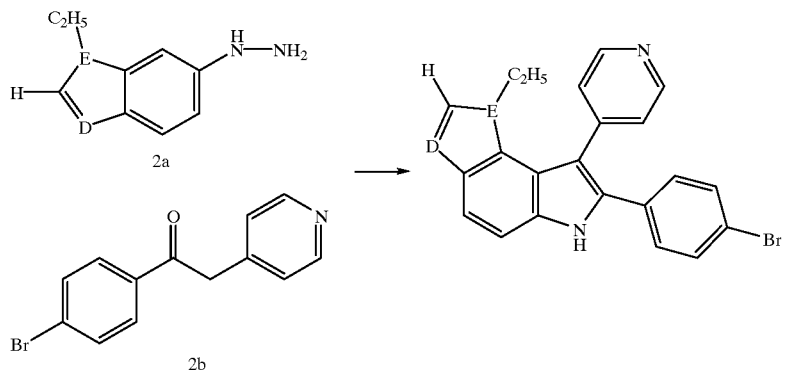

3. Second Embodiment of Formula I

Scheme 3 can be used to prepare the compound of Formula I, wherein A is carbon, ring 1 has a 4-chloro substituent, and B is nitrogen. The hydrazinobenzimidazole 3a, is coupled with the 2-phenyl-1-pyridyl substituted ethanone, 3b, in a suitable solvent such as ethylene glycol at about 90° C. for about 1–3 hours to give the illustrated compound. Similar compounds of Formula I may be prepared by varying the ethanone and benzimidazole starting materials. The ethanone starting material, 3b, is prepared from the addition, hydrolysis and subsequent decarboxylation of a phenylacetonitrile derivative and methylisonicotinate. (Lantos, I. et al., Synthetic and Mechanistic Studies on the Preparation of Pyridyl-Substituted Imidazothiazoles, *J. Org. Chem.*, 1988, 53, 4223–27.)

SCHEME 3

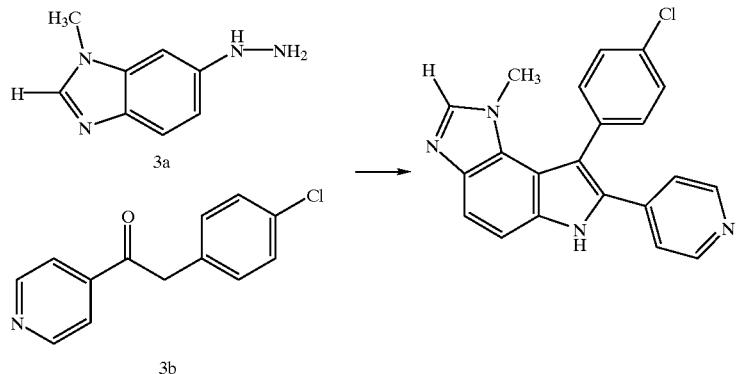

4. 1,6-Dihydro-7-(4-fluorophenyl)-8-(4-pyridyl)-2-phenylmethyl-pyrrolo [3,2-e] Benzimidazole

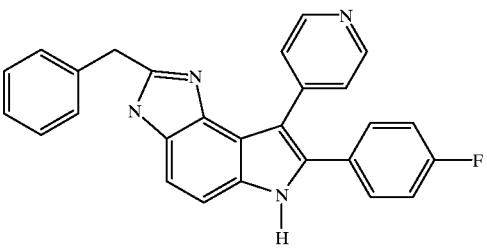

2-Benzyl-5-hydrazinobenzimidazole dihydrochoride (7.62 g) and 1-(4-fluoro-phenyl)-2-(4-pyridinyl)ethanone (5.27 g) were dissolved in ethylene glycol (70 mL). The mixture was heated and stirred at 90° C. for 1 hour, and at 160° C. for 3 hours. The resulting mixture was cooled to room temperature, poured into water (500 ml), and neutralized with solid $K_2CO_3$. The aqueous phase was extracted with ethyl acetate (2×600 ml). The organic layers were separated, combined, washed with water (2×300 ml) and brine (200 ml), dried ($Na_2SO_4$) and concentrated in vacuo. The concentrated solution was filtered through an 8×2 inch plug of silica gel using 100% ethyl acetate (2 L) as eluent. Concentration in vacuo gave an off-white solid (2.65 g). Recrystallization from ethanol gave a white solid: mp 167–69° C.; $^1$H NMR (300 MHz, DMSO-d6): d 12.20 (1H, s), 11.84 (1H, s), 8.48 (2H, br s), 7.62 (2H, br s), 7.45 (2H, br t), 7.36–7.20 (9H, m), 4.20 (2H, s); MS m/s MH$^+$ 419; Anal. Calcd. for $C_{27}H_{19}FN_4$.38H$_2$O C 76.35, H 4.68, N 13.19. Found C 76.29, H 4.69, N 13.15. 1.38 wt % H$_2$O found by Karl Fisher.

C. Assays

1. In Vitro Enzyme Assay

The biological activities of the compounds of this invention were demonstrated by in vitro assays. As discussed previously, agents which inhibit the activity of the enzyme p38 inhibit the production of the inflammatory cytokines TNF-α and IL-1. Compounds of the invention were measured for their ability to inhibit the activity of p38 by the following in vitro assay.

A solution (38 μL) of purified recombinant p38 (where the amount of enzyme was determined empirically considering the linear range of the assay and the acceptable signal to noise ratio; 6×His-p38 expressed in *E. coli*), myelin basic protein substrate (also determined empirically), and a buffer of pH 7.5 (Hepes:25 mM, MgCl$_2$:10 mM, MnCl$_2$:10 mM) were added to 92 wells of a 96-well round bottom polypropylene plate. The remaining wells were used for control ("CTRL") and background ("BKG").

The CTRL was prepared with the enzyme, substrate buffer and 2% DMSO, and the BKG was prepared with substrate buffer and 2% DMSO. A solution (12 μL) of the test compound in DMSO (compounds were diluted to 125 μM in 10% DMSO/H$_2$O and assayed at 25 μM where the final DMSO concentration was 2%) was added to the testing wells. The ATP/$^{33}$P-ATP solution (10 μL: containing 50 μM unlabeled ATP and 1 μCi $^{33}$P-ATP) was added to all wells and the completed plates were mixed and incubated at 30° C. for 30 minutes. Ice-cold 50% TCA/10 mM sodium phosphate (60 μL) was added to each well and the plates were kept on ice for 15 minutes.

The contents of each well were transferred to the wells of a 96-well filterplate (Millipore, MultiScreen-DP) and the filterplate was placed on a vacuum manifold, fitted with a waste collection tray. The wells were washed five times with 10% TCA/10 mM sodium phosphate (200 μL) under vacuum. MicroScint-20 scintillant was added, the plates were sealed using Topseal-S sheets and counted in a Packard TopCount scintillation counter using a $^{33}$P liquid program with color quench correction, where the output is in color quench-corrected cpm.

The % inhibition of the test compounds was calculated by the following formula: % inhibition=[1−(sample -BKG)/(CTRL-BKG)]×100. Compound 1 inhibited 44% of the activity of p38 at 20 μM.

2. In Vitro Cell Assay

In addition to the enzyme assay, many of the compounds of the invention were tested in an in vitro whole cell assay using peripheral blood mononuclear cells ("PBMC") which were obtained from human blood as follows. Freshly obtained venous blood was anticoagulated with heparin, diluted with an equal volume of phosphate buffered saline ("PBS") and placed in a sterile tube or other container. Aliquots (30 mL) of this mixture were transferred to centrifuge tubes which were underlaid with Ficoll-Hypaque (15 mL). The prepared tubes were centrifuged at 400×g without braking for 30 minutes at room temperature. Approximately ½ to ⅔ of the platelet layer above the mononuclear cell band was removed with a pipet. The majority of the mononuclear cell layer was carefully removed using a pipet and these PBMC's were diluted with PBS and spun at 600×g for 15 minutes. The resulting PBMC's were washed with another portion of PBS and spun at 400×g for 10 minutes at room temperature. The recovered pellets were diluted in low endotoxin RPMI/1% FCS culture medium and gave a cell concentration of 0.5–2.0×10$^6$ PBMC/mL. A small volume of the suspension was removed for counting on a hemocytometer and the remaining preparation was centrifuged at 200×g for 15 minutes at room temperature. The recovered pelleted PBMC's were resuspended in RPMI/1% FCS to a concentration of 1.67×10$^6$/mL.

To run the assay, the PBMC suspension (180 μL) was transferred to duplicate wells of a 96-well flat-bottom microtiter plate and incubated for 1 hour at 37° C. A solution of test compound (10 μL: prepared at 20×the desired final concentration) was added to each well and the plate was incubated for 1 hour at 37° C. A solution (10 μL) of LPS in RPMI/1% FCS (200 ng/mL) was added and the wells were incubated overnight at 37° C. The supernatant (100 μL) was removed from each well and diluted with RPMI/1% FCS (400 μL). The samples were analyzed for TNF-α using a commercial ELISA kit (Genzyme).

The anti IL-1β activity of certain compounds of the invention was determined by the following in vitro assay. Plastic-adherent cells were prepared for PBMC. Briefly, PBMCs were added to the wells of a 96-well plate as above, incubated for 1 h at 37° C., and the adherent cells prepared by gently re-suspending the non-adherent cells with a pipettor, removing and discarding the supernatant, and gently washing the wells 3 times with 200 μL of culture medium. Additional culture medium (180 μL) was added to the wells after the final wash. Compound addition, LPS stimulation, incubation and supernatant harvest were as for TNF-α. Supernatants were assayed for interleukin-1β using a commercial ELISA (Genzyme) and IC$_{50}$ values were determined. Compound 1 (described below) inhibited the production of IL-1β at IC$_{50}$ values of 400, 124, and 87 nM.

3. In Vivo Assay

The ability of the compounds of Formula I to inhibit LPS-induced TNF-α production was demonstrated in the following in vivo rodent assays. Mice (BALB/cJ females, Jackson Laboratories) or rats (Lewis males, Charles River) were fasted for 30 minutes prior to oral dosing with 5–10 mL/kg of test compound at 5–50 mg/kg. Thirty minutes after dosing, the animals were injected intraperitoneally with LPS at 1 mg/kg and returned to their cages for 1 hour. Animals were anesthetized by CO$_2$, exsanguinated by cardiac puncture and whole blood collected (0.1–0.7 mL). The blood was allowed to clot and serum was transferred to a centrifuge tube. This sample was centrifuged, serum was collected, aliquoted and frozen at −80° C. Samples were tested by commercial ELISA's for TNF-α (Endogen for mouse TNF-α and Biosource for rat TNF-α). In the mouse, compound 1 inhibited TNF-α 91% at 25 mg/kg and 74% at 10 mg/kg.

Certain compounds of the invention are listed in Tables A and B. The compounds were tested for their ability to inhibit TNF-α in vitro. The data are listed as an IC$_{50}$ or as the % inhibition at a given concentration.

TABLE A

[Structure: pyrrolo-benzimidazole core with R1, R2, R3 substituents, 4-pyridyl and 4-fluorophenyl groups]

| Cpd. | R1 | R2 | R3 | TNF-α IC50 nm |
|---|---|---|---|---|
| 1 | PhCH2 | H | # | 7.0 |
| 2 | Ph | H | # | 20.0 |
| 3 | H | H | # | 60.0 |
| 4 | CH3(CH2)3 | H | # | 45.0 |
| 5 | H | Ph(CH2)3 | # | 1000 |
| 6 | H | (CH3)2N(CH2)2 | # | 2500 |
| 7 | Ph(CH2)2 | H | # | 50.0 |
| 8 | H | # | Ph(CH2)3 | 200 |

# = absent

TABLE B

[Structure: pyrrolo-benzimidazole core with R1, R2, R3 substituents, 4-fluorophenyl and 3-pyridyl groups]

| Cpd. | R1 | R2 | R3 | IC50 nm |
|---|---|---|---|---|
| 9 | H | H | # | 15.0 |
| 10 | PhCH2 | H | # | >400 |
| 11 | H | Ph(CH2)3 | # | 0% @ 400 nM |

What is claimed is:

1. A compound having the structure

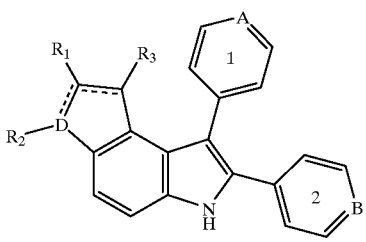

or a pharmaceutically acceptable salt thereof, wherein:
(a) $R_1$, $R_2$ and $R_3$ are independently selected from the group consisting of (i) hydrogen, (ii) $C_{1-5}$alkyl, (iii) $C_{1-5}$alkylamino, (iv) $diC_{1-5}$alkylamino, (v) a phenyl substituted with one or more of hydrogen, halogen, $C_{1-5}$alkyl, and trihalo$C_{1-5}$alkyl, and (vi) a phenyl$C_{1-5}$alkyl substituted with one or more of hydrogen, halogen, $C_{1-5}$alkyl, and trihalo$C_{1-5}$alkyl;

(b) rings 1 and 2 are each independently substituted with one or more substituents selected from the group consisting of hydrogen, halogen, $C_{1-5}$alkyl, and trihalo$C_{1-5}$alkyl;

(c) A and B are independently nitrogen or carbon, at least one of A and B being nitrogen;

(d) D and E are nitrogen, with the proviso that (i) a double bond exists between the non-aryl carbon and either D or E, (ii) $R_2$ is absent if the double bond exists between the non-aryl carbon and D, and (iii) $R_3$ is absent if the double bond exists between the non-aryl carbon and E; and (e) the compound is neither 1,6-dihydro-7-(4-pyridyl)-8-(4-fluorophenyl)-2-phenylmethyl-pyrrolo[3,2-e]benzimidazole, nor 3,6-dihydro-8-(4-fluorophenyl)-3-(3-phenylpropyl)-7-(4-pyridyl)-pyrrolo[3,2-e]benzimidazole.

2. The compound of claim 1, wherein A is nitrogen and B is carbon.

3. The compound of claim 1, wherein D, E and A are nitrogen and B is carbon.

4. The compound of claim 1, wherein the compound is 1,6-dihydro-7-(4-fluorophenyl)-8-(4-pyridyl)-2-phenyl-pyrrolo[3,2-e]benzimidazole.

5. The compound of claim 1, wherein the compound is 1,6-dihydro-7-(4-fluorophenyl)-8-(4-pyridyl)-2-butyl-pyrrolo[3,2-e]benzimidazole.

6. The compound of claim 1, wherein the compound is 1,6-dihydro-7-(4-fluorophenyl)-8-(4-pyridyl)-2-(2-phenylethyl)-pyrrolo[3,2-e]benzimidazole.

7. The compound of claim 1, wherein the compound is 1,6-dihydro-7-(4-pyridyl)-8-(4-fluorophenyl)-pyrrolo[3,2-e]benzimidazole.

8. The compound of claim 1, wherein the compound is 1,6-dihydro-7-(4-fluorophenyl)-8-(4-pyridyl)-2-phenylmethyl-pyrrolo[3,2-e]benzimidazole.

9. A pharmaceutical composition comprising the compound of claim 1, and a pharmaceutically acceptable carrier.

10. A method of treating a subject having an inflammatory disease, which comprises administering to the subject a therapeutically effective dose of the pharmaceutical composition of claim 9.

11. The method of claim 10, wherein the disease is selected from the group consisting of rheumatoid arthritis, insulin-dependent diabetes mellitus, multiple sclerosis, myasthenia gravis, Crohn's disease, autoimmune nephritis, primary biliary cirrhosis and psoriasis, acute pancreatitis, allograph rejection, allergic inflammation, inflammatory bowel disease, septic shock, osteoporosis, osteoarthritis, and cognitive deficits induced by neuronal inflammation.

12. The method of claim 11, wherein the disease is rheumatoid arthritis.

* * * * *